US00PP25282P2

(12) United States Plant Patent
Oates

(10) Patent No.: US PP25,282 P2
(45) Date of Patent: Feb. 3, 2015

(54) ***ECHEVERIA* PLANT NAMED 'ECRRE02-0'**

(50) Latin Name: *Echeveria gibbiflora*
Varietal Denomination: ECRRE02-0

(71) Applicant: John David Oates, Tura Beach (AU)

(72) Inventor: John David Oates, Tura Beach (AU)

( * ) Notice: Subject to any disclaimer, the term of this patent is extended or adjusted under 35 U.S.C. 154(b) by 30 days.

(21) Appl. No.: 13/987,156

(22) Filed: Jul. 3, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Anne Grunberg
(74) *Attorney, Agent, or Firm* — Cassandra Bright

(57) ABSTRACT

A new and distinct *Echeveria* cultivar named 'ECRRE02-0' is disclosed, characterized by tight rosulate plant form, unique heavily crenulated leaf margins. Foliage is colored greyed-green with red margins and greyed-red margin flushing. The new variety is an *Echeveria*, normally produced as an ornamental garden or container plant.

1 Drawing Sheet

Latin name of the genus and species: *Echeveria gibbiflora*.
Variety denomination: 'ECRRE02-0'.

BACKGROUND OF THE INVENTION

The new *Echeveria* cultivar is a product of a planned breeding program conducted by the inventor, John Oates, in Thirlmere, Australia. The objective of the breeding program was to produce new *Echeveria* varieties for ornamental commercial applications. The new variety is a product of cross breeding that occurred on May 5, 2005, at a commercial nursery in Thirlmere, Australia.

The seed parent is the unpatented, proprietary seedling variety of *Echeveria gibbiflora*×*derenbergii*, 'Line 540'. The pollen parent is the unpatented, proprietary seedling variety *Echeveria gibbiflora*, 'Line 546'. The new variety was discovered during October of 2006 by the inventor in a group of seedlings resulting from the 2005 crossing, in a commercial nursery in Thirlmere, Australia.

Asexual reproduction of the new cultivar has been performed by tissue culture. This was first performed at a laboratory in Tumbi Umbi, Australia in March of 2008 and has shown that the unique features of this cultivar are stable and reproduced true to type in 15 successive generations.

SUMMARY OF THE INVENTION

The cultivar 'ECRRE02-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECRRE02-0'. These characteristics in combination distinguish 'ECRRE02-0' as a new and distinct *Echeveria* cultivar:

1. Leaf margin colored red with greyed-red flushing.
2. Leaf color fades from bright green to pale green with an increase in temperature.

3. Rosulate plant form, no branching.
4. Leaf margin heavily crenulated.

PARENT COMPARISON

Plants of the new cultivar 'ECRRE02-0' are similar to plants of the seed parent *Echeveria gibbiflora*×*derenbergii*, 'Line 540' in most horticultural characteristics, however, plants of the new cultivar 'ECRRE02-0' produce a leaf margin which is crenulated, compared to the undulating margin of the seed parent. Additionally, 'ECRRE02-0' also produces leaf margins of a somewhat different coloration than those of the seed parent.

Plants of the new cultivar 'ECRRE02-0' are similar to plants of the pollen parent; *Echeveria gibbiflora* 'Line 546' in most horticultural characteristics, however, plants of the new cultivar 'ECRRE02-0' produce a leaf margin which is crenulated, compared to the undulating margin of the pollen parent. Additionally 'ECRRE02-0' also produces leaf margins of a different coloration than those of the seed parent.

COMMERCIAL COMPARISON

'ECRRE02-0' can be compared to the commercial variety *Echeveria gibbiflora* 'ECRPI01-0', filed concurrently, having application Ser. No. 13/987,157. Plants of 'ECRRE02-0' are similar to plants of 'ECRPI01-0' in most horticultural characteristics, however, plants of 'ECRRE02-0' produce leaves with a more crenulated margin than 'ECRPI01-0'. Overall leaf aspect is less undulating in 'ECRRE02-0' than the leaf aspect of 'ECRPI01-0'. Additionally, margin coloration is somewhat different between the new varieties.

'ECRRE02-0' can be compared to the commercial variety *Echeveria gibbiflora* 'ECRAQ03-0', filed concurrently, having application Ser. No. 13/987,155. Plants of 'ECRRE02-0' are similar to plants of 'ECRAQ03-0' in most horticultural characteristics, however, plants of 'ECRRE02-0' produce leaves with a crenlated margin, compared to the tightly undulating margin of 'ECRAQ03-0'. Additionally, foliage coloration is significantly different.

BRIEF DESCRIPTION OF THE PHOTOGRAPH

The accompanying photograph in FIG. 1 illustrates in full color a typical plant of 'ECRRE02-0'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ECRAQ03-0' plants grown in a greenhouse in Oxnard, Calif. The growing temperature ranged from approximately 15° C. to 28° C. during the day and from 12° C. to 22° C. during the night. General light conditions are bright, normal sunlight. Measurements and numerical values represent averages of typical plant types. Measurements were taken from plants grown in warm temperatures, during Spring and Summer.
Botanical classification: *Echeveria gibbiflora* 'ECRRE02-0'.

PROPAGATION

Propagation method: Vegetative divisions or tissue culture.

PLANT

Age of plant described: Approximately 14 months from tissue culture.
Container size: 1 gallon nursery container.
Growth habit: Central Rosette.
Height: Approximately 14 cm to top of highest leaf. Approximately 40 cm to top of inflorescence.
Plant spread: Approximately 29 cm.
Growth rate: Slow.
Branching characteristics: To date, only a single rosette, without branches observed.

FOLIAGE

Leaf:
- *Arrangement*.—Rosette.
- *Average length*.—Approximately 13 cm.
- *Average width*.—Approximately 15 cm.
- *Shape of blade*.—Spatulate.
- *Apex*.—Rounded crenulate.
- *Base*.—Obuse.
- *Margin*.—Crenulate, intense ruffling.
- *Aspect*.—Deeply undulating.
- *Texture of top surface*.—Glabrous.
- *Texture of bottom surface*.—Glabrous.
- *Quantity of leaves per plant*.—Approximately 10 large leaves, and 8 smaller immature inner leaves.
- *Color*.—Young foliage upper side: Near RHS Greyed-Green 194A; margin near RHS Red 47A. Young foliage under side: Near RHS Greyed-Green 194A; margin near RHS Red 47A. Mature foliage upper side: Near RHS Greyed-Green 194A; margin near RHS Red 47A. Flushing along margin near RHS Greyed-Red 186B. Mature foliage under side: Near RHS Greyed-Green 194A; margin near RHS Red 47A. Flushing along margin near RHS Greyed-Red 186B.

Venation:
- *Type*.—Linear.
- *Venation color upper side*.—Indistinguishable from foliage.
- *Venation color under side*.—Indistinguishable from foliage.

FLOWER

Flowering season: Very irregular, one flower spike observed during Summer, during the previous year of testing. Flowers aborted in the bud stage and did not open.
Inflorescence type and habit: Heterothetic compound raceme.
Quantity of flower buds: Approximately 25 buds per flowering stem.
Total inflorescence size, including scape:
- *Height*.—Approximately 32 cm.
- *Width*.—Approximately 8 cm.
- *Individual Racemes per inflorescence*.—Average 5.

Individual raceme size, including peduncle:
- *Height*.—Approximately 3 cm.
- *Width*.—Approximately 3.2 cm.
- *Individual Flowers per raceme*.—Average 4 or 5.

Individual flowers: Flowers have not been observed to open, flower buds aborting.
Bud:
- *Shape*.—Conical.
- *Length*.—Approximately 0.9 cm.
- *Diameter*.—Approximately 0.5 cm. Color: Base near RHS Greyed-Green 193C, mid section near RHS Red-Purple 59D, but lighter. Apex near RHS Red-Purple 59C.

Sepals:
- *Length*.—Approximately 0.8 cm.
- *Width*.—Approximately 0.4 cm.
- *Shape*.—Deltoid.
- *Apex*.—Acute.
- *Base*.—Blunt.
- *Texture*.—Glabrous, fleshy.
- *Color*.—Near RHS Greyed-Green 193B, Margin and Apex flushed near RHS Red-Purple 59C.

Pedicels:
- *Length*.—Approximately 0.3 cm.
- *Width*.—Approximately 0.2 cm.
- *Aspect*.—Approximately 25° angle, or less to peduncle, straight.
- *Color*.—Near RHS Greyed-Red 181B.
- *Strength*.—Very strong.
- *Texture*.—Glabrous, fleshy.

Peduncles:
- *Length*.—Average 2.0 cm.
- *Width*.—Approximately 0.4 cm.
- *Aspect*.—Approximately 90° angle, to scape, deeply recurved, nearly scorpoid.
- *Color*.—Near RHS Red 47D.
- *Strength*.—Very strong.
- *Texture*.—Glabrous, fleshy.

Scape:
- *Length*.—Approximately 28 cm to bottom of first peduncle.
- *Width*.—Approximately 1.1 cm.
- *Angle*.—Arising at approximately an 80° angle from foliar rosette.
- *Strength*.—Very strong.

*Color*.—Near RHS Greyed-Green 195C, moderate to slight flushing with near RHS Red 47B.

Scape scales:

*Quantity*.—Approximately 8.

*Length*.—Average 2.7 cm.

*Width*.—Approximately 1.5 cm.

*Aspect*.—Approximately 15° angle to scape, straight or somewhat cupped.

*Color*.—Near RHS Greyed-Purple N187B and 187C. Flushed near RHS Red-Purple 59B.

*Texture*.—Glabrous, fleshy.

Fragrance: None.

REPRODUCTIVE ORGANS

Not observed to date.

OTHER CHARACTERISTICS

Seeds and fruits: No seeds-fruits detected to date.

Disease/pest resistance: Neither resistance nor susceptibility to the normal diseases and pests of *Echeveria* have been observed.

Temperature tolerance: Tolerates temperatures from approximately 0° C. to at least 40° C.

What is claimed is:

1. A new and distinct cultivar of *Echeveria* plant named 'ECRRE02-0' as herein illustrated and described.

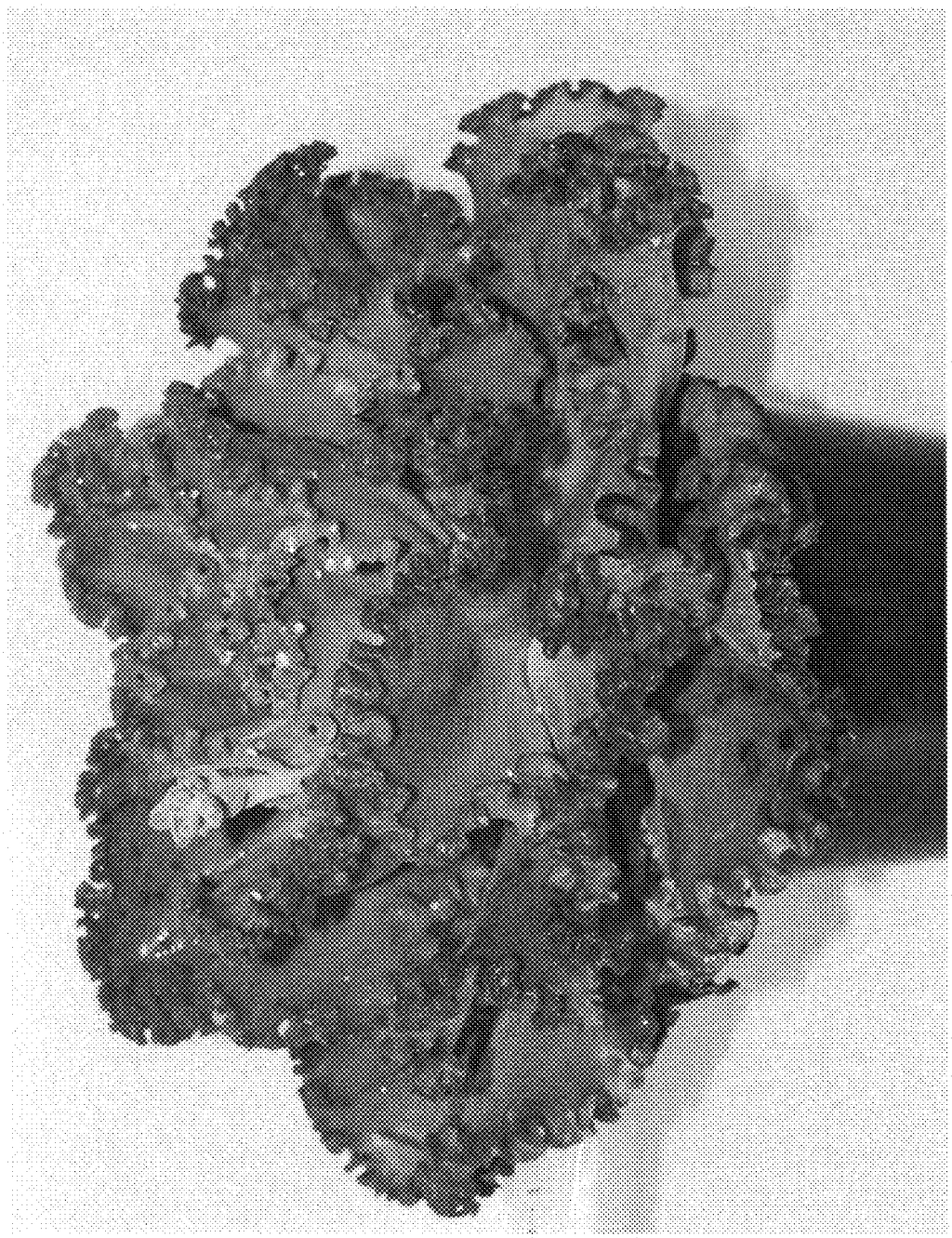

* * * * *